(12) United States Patent
Saitoh et al.

(10) Patent No.: US 6,777,211 B1
(45) Date of Patent: Aug. 17, 2004

(54) PROCESS FOR PRODUCING HYDROXYLATED FATTY ACID AND DELTA-LACTONE

(75) Inventors: Chiaki Saitoh, Inashiki-gun (JP); Yukiko Masuda, Tsukuba (JP); Atsushi Yashiro, Tokyo (JP); Hiroki Ishiguro, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/019,957
(22) PCT Filed: Jul. 7, 2000
(86) PCT No.: PCT/JP00/04535
§ 371 (c)(1), (2), (4) Date: Jan. 7, 2002
(87) PCT Pub. No.: WO01/04339
PCT Pub. Date: Jan. 18, 2001

(30) Foreign Application Priority Data

Jul. 7, 1999 (JP) .......................................... 11/192684

(51) Int. Cl.[7] ................................................ C12P 17/06
(52) U.S. Cl. ....................................................... 435/125
(58) Field of Search ......................................... 435/125

(56) References Cited

U.S. PATENT DOCUMENTS

| 5,168,054 A | 12/1992 | Cardillo et al. |
| 5,215,901 A | 6/1993 | Boog et al. |

FOREIGN PATENT DOCUMENTS

| JP | 60-66991 | 4/1985 |
| JP | 60-100508 | 6/1985 |

OTHER PUBLICATIONS

Hudson et al., "Hydration of linoleic acid by bacteria isolated from ruminants", FEMS Microbiology Letters 169 : 277–282 (1998).*
Fox et al., "The biosynthesis of oxylipins of linoleic and arachidonic acids by the sewage fungus Leptomitus lacteus, including the identification of 8 R–hydroxy–9Z, 12Z–octadecadienoic acid", Lipids 35 (1) :23–30 (2000).*
Cardillo, et al., "Stereochemistry of the Microbial Generation . . . ", *The Journal of Organic Chemistry*, vol. 56, No. 18, Aug. 30, 1991, pp. 5237–5239.
Gatfield, et al., "Some Aspects of the Microbiological Production of Flavor . . . ", *Chem. Mikrobiol. Technol. Lebensm.*, 15 (5/6), pp. 165–170, 1993.
Endrizzi, et al;., "Production of Lactones and Peroxisomal Beta–Oxidation in Yeasts", *Critical Reviews in Biotechnology*, 16(4), pp. 301–329, 1996.
Seo, et al., "Hydration of Squalene and Oleic Acid by Corynebacterium sp. S–401", *Agric. Bio. Chem.*, 45(9), pp. 2025–2030, 1981.
Wallen, et al., "The Microbiological Production of 10–Hydroxystearic Acid from Oleic Acid", *Archives of Biochemistry and Biophysics*, 99, pp. 249–253, 1962.
Teranishi, et al., "Flavor Precursors, Thermal and Enzymatic Conversions", ACS Symposium Series 490, pp. 47–57, 1991.
Cardillo, et al., "On the Mode of Conversion of Racemic . . . ", *J. Org. Chem.* 1989, 54, pp. 4979–4980.
Albrecht, et al., "Studies on the Biosynthesis of Aliphatic Lactones in *Sporobolomyces odorus* . . . ", *J. Org. Chem.* 1992, 57, pp. 1954–1956.
P. Thomas, "Identification of Some Enteric Bacteria Which Convert Oleic Acid to Hydroxystearic Acid in Vitro" Gastroenterology, vol. 62, No. 3, pp. 430–435, 1972.

* cited by examiner

*Primary Examiner*—Sandra E. Saucier
(74) *Attorney, Agent, or Firm*—Antonelli, Terry, Stout & Kraus, LLP

(57) ABSTRACT

The process which comprises causing cells or a culture of a microorganism having the activity to introduce hydroxy into the [n-5]-position (n is an even number of 10 or more) and hydrogen into the [n-6]-position of a straight-chain fatty acid having n carbon atoms wherein at least the [n-6]-position is a double bond to make the [n-6]-position a single bond or a treated matter thereof to act on a straight-chain fatty acid having n carbon atoms wherein at least the [n-6]-position is a double bond or a composition containing the fatty acid to form an [n-5]-hydroxy fatty acid wherein the [n-6]-position is a single bond, causing cells or a culture of a microorganism having the activity to β-oxidize an [n-5]-hydroxy fatty acid wherein the [n-6 ]-position is-a single bond or a treated matter thereof to act on the formed [n-5]-hydroxy fatty acid, and recovering the formed δ-lactones.

12 Claims, No Drawings

PROCESS FOR PRODUCING HYDROXYLATED FATTY ACID AND DELTA-LACTONE

TECHNICAL FIELD

The present invention relates to a process for producing [n-5]-hydroxy fatty acids (n is an even number of 10 or more) wherein the [n-6]-position is a single bond from straight-chain fatty acids having n carbon atoms wherein at least the [n-6]-position is a double bond. The present invention also relates to a process for producing β-lactones from the fatty acids and compositions containing δ-lactones.

BACKGROUND ART

Lactones are important compounds which are widely used as food additives because of their property of imparting preferable flavors such as a fruit flavor and a milk flavor. However, as lactones are contained in natural materials only at low concentrations, chemically synthesized products are generally used.

As for the process for producing lactones using microorganisms, it is known that 10-hydroxyoctadecanoic acid, a precursor of δ-dodecalactone, is formed from oleic acid by the activity of microorganisms such as lactic acid bacteria and bifidobacteria.[Gastroenterology, 62, 430 (1972)], bacteria belonging to the genus Corynebacterium [Agricultural and Biological Chemistry, 45, 2025(1981)] and bacteria belonging to the genus Pseudomonas [Archives of Biochemistry and Biophysics, 99, 249(1962)]. It is also known that hydroxylated fatty acids such as 10-hydroxyoctadecanoic acid and ricinoleic acid in castor oil can be converted into δ-lactones by the activity of yeasts (Japanese Published Unexamined Patent Application Nos. 66991/85 and 100508/85).

*Sporobolomyces odorus*, a yeast which produces lactones, is known to produce δ-decalactone from linoleic acid. From the fact that δ-decalactone is produced from 13-hydroxy-9Z,11E-octadecadienoic acid (coriolic acid), it is presumed that the yeast produces coriolic acid as an intermediate [ACS SYMPOSIUM SERIES, Flavor Precursors, 490, 46(1992)].

A method is known for converting coriolic acid as a precursor obtained by reduction of hydroperoxide obtained by subjecting linoleic acid to photooxidation or treatment with soybean lipoxygenase into δ-decalactone by the activity of bacteria belonging to the genus Cladosporium or yeasts (Japanese Published Unexamined Patent Application No. 187387/91). Also known is a method for converting coriolic acid contained in seed oil of *Coriaria nepalencis* and 11-hydroxypalmitic acid extracted from the roots of Mexican jalap as precursors into δ-decalactone by the activity of bacteria belonging to the genus Cladosporium [Journal of organic Chemistry, 54, 4979 (1989)] or yeasts [Journal of organic Chemistry, 57, 1954(1992) and Japanese Published Unexamined Patent Application No. 219886/91].

However, there has not been reported a process for producing δ-decalactone and jasmine lactone respectively from 13-hydroxy-9-ocatadecenoic acid and 13-hydroxy-9,15-octadecadienoic acid formed respectively from linoleic acid and α-linolenic acid by the activity of microorganisms.

DISCLOSURE OF THE INVENTION

An object of the present invention is to provide a process for producing [n-5]-hydroxy fatty acids (n is an even number of 10 or more) wherein the [n-6]-position is a single bond from straight-chain fatty acids having n carbon atoms wherein at least the [n-6]-position is a double bond using a microorganism. Another object of the present invention is to provide a process for producing δ-lactones from the fatty acids using a microorganism and to provide compositions containing δ-lactones.

The present invention relates to a process for producing an [n-5]-hydroxy fatty acid (n is an even number of 10 or more) wherein the [n-6]-position is a single bond, which comprises causing cells or a culture of a microorganism having the activity to introduce hydroxy into the [n-5]-position and hydrogen into the [n-6]-position of a straight-chain fatty acid having carbon atoms wherein at least the [n-6]-position is a double bond to make the [n-6]-position a single bond (hereinafter referred to as the first microorganism) or a treated matter thereof to act on a straight-chain fatty acid having n carbon atoms wherein at least the [n-6]-position is a double bond or a composition containing the fatty acid to form the [n-5]-hydroxy fatty acid wherein the [n-6]-position is a single bond, and recovering the formed [n-5]-hydroxy fatty acid wherein the [n-6]-position is a single bond.

The present invention also relates to 13-hydroxy-6,9-octadecadienoic acid represented by the following formula (I):

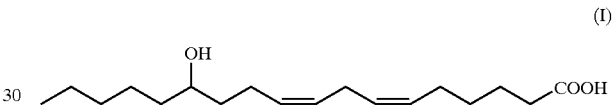

The present invention also relates to a process for producing a δ-lactone, which comprises causing cells or a culture of the first microorganism or a treated matter thereof to act on a straight-chain fatty acid having n carbon atoms (n is an even number of 10 or more) wherein at least the [n-6]-position is a double bond or a composition containing the fatty acid to form an [n-5]-hydroxy fatty acid wherein the [n-6]-position is a single bond, then causing cells or a culture of a microorganism having the activity to β-oxidize an [n-5]-hydroxy fatty acid wherein the [n-6]-position is a single bond (hereinafter referred to as the second microorganism) or a treated matter thereof to act on the formed [n-5]-hydroxy fatty acid, and recovering the formed δ-lactone.

The present invention also relates to a process for producing a composition containing a δ-lactone, which comprises causing cells or a culture of the first microorganism or a treated matter thereof to act on a composition containing a straight-chain fatty acid having n carbon atoms (n is an even number of 10 or more) wherein at least the [n-6]-position is a double bond to form an [n-5]-hydroxy fatty acid wherein the [n-6]-position is a single bond in the composition, and then causing cells or a culture of the second microorganism or a treated matter thereof to act on the formed [n-5]-hydroxy fatty acid.

The present invention further relates to a process for producing a food containing a δ-lactone, which comprises adding the δ-lactones or the composition containing the δ-lactones produced by the above process to a food.

In the present invention, the expression "the [n-m]-position is a double bond" means that the [n-m]-position and the [n-(m-1)]-position are bonded by a double bond.

The straight-chain fatty acids having n carbon atoms (n is an even number of 10 or more) wherein at least the [n-6]-position is a double bond of the present invention include monoenoic fatty acids, dienoic fatty acids and trienoic fatty acids wherein the [n-6]-position is a double bond, preferably a cis-form double bond.

Preferred polyenoic fatty acids (e.g., dienoic fatty acids and trienoic fatty acids) are nonconjugated polyenoic fatty acids wherein the [n-9]-position is a double bond, specifically a cis-form double bond. When n is 12 or more, fatty acids wherein the [n-10]- and lower positions are single bonds are desirable for the formation of δ-lactones.

There is no upper limit to n insofar as n is an even number of 10 or more, but n is preferably 10 to 32, more preferably 12 to 26, and most preferably 16 to 22.

Examples of the monoenoic fatty acids include decenoic acid, dodecenoic acid, tetradecenoic acid, hexadecenoic acid, octadecenoic acid, eicosenoic acid, docosenoic acid, tetracosenoic acid, hexacosenoic acid, octacosenoic acid, triacontenoic acid, dotriacontenoic acid and tetratriacontenoic acid.

Examples of the dienoic fatty acids include decadienoic acid, dodecadienoic acid, tetradecadienoic acid, hexadecadienoic acid, octadecadienoic acid, eicosadienoic acid, docosadienoic acid, tetracosadienoic acid, hexacosadienoic acid, octacosadienoic acid, triacontadienoic acid, dotriacontadienoic acid and tetratriacontadienoic acid.

Examples of the trienoic fatty acids include decatrienoic acid, dodecatrienoic acid, tetradecatrienoic acid, hexadecatrienoic acid, octadecatrienoic acid, eicosatrienoic acid, docosatrienoic acid, tetracosatrienoic acid, hexacosatrienoic acid, octacosatrienoic acid, triacontatrienoic acid, dotriacontatrienoic acid and tetratriacontatrienoic acid.

Specific examples of these fatty acids include 4-decenoic acid, 7,10-hexadecadienoic acid, 6,10-hexadecadienoic acid, 12-octadecenoic acid, linoleic acid, α-linolenic acid, γ-linolenic acid, 11,14-eicosadienoic acid, 5,11,14-eicosatrienoic acid, 8,11,14-eicosatrienoic acid, bishomo-γ-linolenic acid, 11,14,17-eicosatrienoic acid, 6,9,12,15-octadecatetraenoic acid, 13,16-docosadienoic acid, 7,10,13,16-docosatetraenoic acid and arachidonic acid. Preferred are linoleic acid, α-linolenic acid and γ-linolenic acid, and more preferred are linoleic acid and α-linolenic acid.

In the present invention, a composition containing the straight-chain fatty acid having n carbon atoms (n is an even number of 10 or more) wherein at least the [n-6]-position is a double bond can also be used. Such compositions include natural oils and fats, foods and hydrolyzates thereof.

Examples of the natural oils and fats include obtusiloba oil, evening primrose seed oil, soybean oil, corn oil, safflower oil, wheat germ oil, rice oil, sesame oil, rapeseed oil, olive oil, linseed oil, milk fat, suet, lard, egg yolk oil, fish oil, seaweed, algae, filamentous fungi, ferns and protozoa.

Examples of the foods include foods, such as soybean milk, prepared by adding the straight-chain fatty acids having n carbon atoms (n is an even number of 10 or more) wherein at least the [n-6]-position is a double bond to foods which do not contain the fatty acids, besides foods containing the straight-chain fatty acids having n carbon atoms (n is an even number of 10 or more) wherein at least the [n-6]-position is a double bond.

Hydrolyzates of natural oils and fats or foods can be obtained by treating natural oils and fats or foods with hydrolase, etc.

An example of the hydrolase is lipase.

There is no specific limit as to the amount of the straight-chain fatty acid having n carbon atoms (n is an even number of 10 or more) wherein at least the [n-6]-position is a double bond contained in the composition, but it is preferably 0.01 to 99 wt %, more preferably 0.1 to 90 wt %.

The δ-lactones of the present invention include δ-lactones represented by the following formula (II):

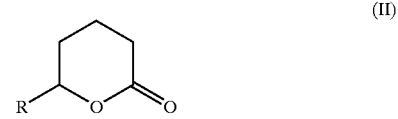

(II)

(wherein R represents n-pentyl or n-pentenyl), for example, δ-decalactone and jasmine lactone.

As the first microorganism of the present invention, any microorganism can be used that has the activity to introduce hydroxy into the [n-5]-position and hydrogen into the [n-6]-position of a straight-chain fatty acid having n carbon atoms (n is an even number of 10 or more) wherein at least the [n-6]-position is a double bond, preferably a cis-form double bond, to make the [n-6]-position a single bond. Preferred is a microorganism which has the activity to introduce hydroxy into the 13-position and hydrogen into the 12-position of linoleic acid, α-linolenic acid or γ-linolenic acid to make the 12-position a single bond.

Examples of the first microorganism include lactic acid bacteria and bifidobacteria. Lactic acid bacteria include those belonging to the genus Pediococcus, e.g. *Pediococcus pentosaceus*. Bifidobacteria include those belonging to the genus Bifidobacterium, e.g. *Bifidobacterium bifidum*. Specifically, *Pediococcus pentosaceus* IFO3891, Pediococcus sp. IFO3778, *Bifidobacterium bifidum* JCM7002, etc. are preferably used.

As the second microorganism of the present invention, any microorganism can be used that has the activity to β-oxidize an [n-5]-hydroxy fatty acid wherein the [n-6]-position is a single bond. For example, yeasts can be used.

Examples of suitable yeasts include microorganisms belonging to the genera Kluyveromyces, Zygosaccharomyces, Pichia and Saccharomyces.

Examples of the microorganisms belonging to the genus Kluyveromyces are *Kluyveromyces marxianus, Kluyveromyces thermotolerans* and *Kluyveromyces wickerhamii*. Examples of the microorganisms belonging to the genus Zygosaccharomyces are *Zygosaccharomvces rouxii, Zygosaccharomyces bailii* and *Zygosaccharomyces cidri*. An example of the microorganism belonging to the genus Pichia is *Pichia jadinii*. An example of the microorganism belonging to the genus Saccharomyces is *Saccharomyces cerevisiae*. As second microorganism, for example, *Kluyveromyces marxianus* IFO1090, *Kluyveromyces thermotolerans* ATCC24177, *Kluyveromyces wickerhamii* ATCC24178, *Zygosaccharomyces rouxii* NFR2007, *Zygosaccharomyces bailii* ATCC8766, *Zygosaccharomyces cidri* ATCC46819, *Pichia jadinii* IFO0987, *Saccharomyces cerevisiae* Kyokai No. 701(sake yeast), etc. are preferably used.

These microorganisms may be used alone or in combination.

In the present invention, any mutants of the above microorganisms obtained by artificial mutation methods such as ultraviolet irradiation, X-ray irradiation, treatment with mutagens and gene manipulation, or by spontaneous mutation may also be used as long as they are microorganisms having the above-described activities.

As the medium for the culturing of these microorganisms, any synthetic or natural medium containing carbon sources, nitrogen sources, inorganic substances and trace components that can be used for general culturing of lactic acid bacteria, bifidobacteria or yeast can be used.

Examples of the carbon sources include starch, dextrin, sucrose, glucose, mannose, fructose, raffinose, rhamnose, inositol, lactose, xylose, arabinose, mannitol, molasses and pyruvic acid. They may be used alone or in combination, preferably in an amount of 1 to 20 g/l.

Examples of the nitrogen sources include ammonium salts such as ammonium chloride, ammonium sulfate, ammonium phosphate, ammonium carbonate and ammonium acetate, nitrates such as sodium nitrate and potassium nitrate, and nitrogen-containing organic substances such as peptone, yeast extract, meat extract, malt extract, corn steep liquor, casein hydrolyzate, soybean powder, vegetable juice, casamino acid and urea. They may be used alone or in combination, preferably in an amount of 1 to 20 g/l.

Examples of the inorganic substances include sodium chloride, potassium chloride, calcium chloride, magnesium sulfate, calcium carbonate, dipotassium hydrogenphosphate, potassium dihydrogenphosphate, ferrous sulfate, calcium chloride, manganese sulfate, zinc sulfate and copper sulfate. They may be used alone or in combination, preferably in an amount of 0.1 to 2 g/l.

Examples of the trace components include vitamins such as biotin, thiamine and nicotinic acid, and amino acids such as β-alanine and glutamic acid. They may be used alone or in combination, preferably in an amount of 0.0001 to 2 g/l.

As the method of culturing, liquid culture, especially submerged spinner culture is preferred. The medium is adjusted to pH 2 to 11, preferably pH 3 to 10, more preferably pH 4 to 8. Culturing is carried out at 10 to 80° C., preferably 10 to 60° C., most preferably 20 to 40° C. generally for 6 hours to 7 days. The pH of the medium is adjusted with aqueous ammonia, an ammonium carbonate solution, etc.

The treated matters of the culture used in the present invention include cells of a microorganism having the activity to introduce hydroxy into the [n-5]-position and hydrogen into the [n-6]-position of a straight-chain fatty acid having n carbon atoms (n is an even number of 10 or more) wherein at least the [n-6]-position is a double bond to make the [n-6]-position a single bond, cultures containing the microorganism and treated matters thereof.

The treated matters of the cells of the microorganism include dried cells, frozen cells, refrigerated cells, freeze-dried cells, heated cells, compressed cells, ultrasonically disrupted cells, products obtained by treating the cells with a surfactant, an organic solvent or a lytic enzyme, immobilized cells, and enzymes obtained from the cells by means of extraction or purification.

An enzyme can be extracted and purified from the cells according to general methods for extraction and purification of a protein. For example, an enzyme can be extracted from the cells using a homogenizer or glass beads, or by ammonia dissolution, the enzyme method, etc., and then purified by means of filtration, centrifugation, salting-out, precipitation with an organic solvent, immune precipitation, etc. as well as dialysis, ultrafiltration, gel filtration, electrophoresis, chromatography using an adsorbent, an affinity adsorbent or molecular sieves, liquid-phase partition, ion exchange, batch method and crystallization, alone or in combination.

As the culture containing the microorganism, a culture obtained after the completion of the culturing can be used as such. Also useful are treated matters obtained by treating the culture by means of concentration, drying, freezing, refrigeration, freeze-drying, heating, pressing, ultrasonic disruption, treatment with a surfactant, an organic solvent or a lytic enzyme, etc. alone or in combination.

The process for producing an [n-5]-hydroxy fatty acid wherein the [n-6]-position is a single bond and the process for producing a δ-lactone are described below.

The [n-5]-hydroxy fatty acid wherein the [n-6]-position is a single bond can be produced by causing cells or a culture of the first microorganism or a treated matter thereof to act on a straight-chain fatty acid having n carbon atoms (n is an even number of 10 or more) wherein at least the [n-6]-position is a double bond or a composition containing the fatty acid, and recovering the formed [n-5]-hydroxy fatty acid wherein the [n-6]-position is a single bond. Details of the process are as follows.

The cells or culture of the first microorganism or a treated matter thereof is subjected to reaction with the straight-chain fatty acid having n carbon atoms (n is an even number of 10 or more) wherein at least the [n-6]-position is a double bond or a composition containing the fatty acid at 10 to 80° C., preferably 20 to 40° C., at pH 2 to 11, preferably pH 3 to 10, more preferably at pH 5 to 8, for 6 hours to 7 days, preferably 1 to 4 days. If necessary, an aqueous medium such as water may be added prior to the reaction.

A buffer, a surfactant, an organic solvent, an antioxidant, etc. may be added to the reaction mixture as may be required.

Examples of the buffer include phosphate buffer and citrate buffer. The concentration of the buffer is preferably 0.01 to 1 mol/l.

Examples of the surfactant include sucrose fatty acid ester, sorbitan fatty acid ester and glycerin fatty acid ester. The concentration of the surfactant is preferably 0.1 to 5%.

An example of the organic solvent is ethanol. The concentration of the organic solvent is preferably 1 to 50 g/l.

Examples of the antioxidant include those applicable to foods, such as α-tocopherol, vitamin E, butylhydroxyanisole (BHA), dibutylhydroxytoluene (BHT) and skim milk powder. The concentration of the antioxidant is preferably 0.01 to 50 g/l.

When the cells of the microorganism are used, reaction is carried out in the following manner. Into 5 to 50 ml of a medium containing carbon sources, nitrogen sources, etc. are inoculated 1 to 3 loopfuls of the cells of the first microorganism, followed by stationary culture for 1 to 5 days. The obtained seed culture is inoculated in an amount of 0.1 to 5% into a straight-chain fatty acid having n carbon atoms (n is an even number of 10 or more) wherein at least the [n-6]-position is a double bond or a composition containing the fatty acid, followed by stationary culture or culturing with stirring at a low speed. Culturing may be carried out at any temperature that allows conversion of the straight-chain fatty acid into an [n-5]-hydroxy fatty acid wherein the [n-6]-position is a single bond, preferably 5 to 40° C. It does not matter whether the first microorganism grows or not by the culturing. The culturing time varies depending upon the conditions, but it is usually 1 to 4 days.

Extraction and detection of the [n-5]-hydroxy fatty acid (n is an even number of 10 or more) wherein the [n-6]-position is a single bond converted from the straight-chain fatty acid having n carbon atoms wherein at least the [n-6]-position is a double bond and contained in the reaction mixture or culture can be carried out according to a conventional method of lipid extraction and a method of lipid detection by thin layer chromatography (TLC). That is, to about 0.2 to 10 ml of the reaction mixture is added about 30 to 80 wt % solvent such as chloroform/methanol (2:1, v/v). After 10 minutes of shaking, the resulting mixture is centrifuged to obtain a solvent layer as a lipid extract. The obtained lipid extract (1 to 20 μl) is spotted on a silica gel-precoated TLC plate and developed using an appropriate solvent system, followed by coloration using an appropriate color developer. The [n-5]-hydroxy fatty acid wherein the [n-6]-position is a single bond can be detected by the coloration on the plate.

As the TLC plate, TLC glass plate 60(No. 5721, Merck & Co., Inc.), or the like may be used.

The [n-5]-hydroxy fatty acid wherein the [n-6]-position is a single bond can be isolated and purified from the reaction mixture or culture by conventional methods for isolation and purification of lipid. That is, the [n-5]-hydroxy fatty acid wherein the [n-6]-position is a single bond can be isolated and purified by carrying out steps such as removal of cells by filtration, centrifugation, etc., extraction of lipid by the use of a solvent such as diethyl ether/toluene (15:85 to 60:40, v/v), adsorption and desorption of lipid by column chromatography or thin layer chromatography using adsorbent resin, silica gel, reversed-phase silica gel, aluminum oxide, cellulose, diatomaceous earth, magnesium silicate, gel filtering agent, ion exchange resin, etc., and partition using an appropriate solvent system. The purity of the obtained fatty acid is about 90 to 100%.

The [n-5]-hydroxy fatty acid wherein the [n-6]-position is a single bond can be detected by thin layer chromatography according to the above-described method.

The [n-5]-hydroxy fatty acid wherein the [n-6]-position is a single bond can be determined, for example, by high performance liquid chromatography under the following conditions.

Apparatus: SPD-10A (Shimadzu Corporation)

Column: TSK-gel ODS-80Ts (Tosoh Corporation)

Mobile phase: solution A: acetonitrile/water/acetic acid (28:72:0.02, v/v/v)
  solution B: acetonitrile/water/acetic acid (52:48:0.02, v/v/v)
  solution A (10 minutes), solution A→solution B (60 minutes, linear concentration gradient), solution B (30 minutes)

Flow rate: 2 ml/minute

Temperature: 40° C.

Detection: UV-200 nm

The [n-5]-hydroxy fatty acid wherein the [n-6]-position is a single bond can be used for production of a δ-lactone which is useful as food additives, etc.

The process for producing a δ-lactone from the [n-5]-hydroxy fatty acid wherein the [n-6]-position is a single bond is described below.

The cells or culture of the second microorganism or a treated matter thereof is subjected to reaction with a reaction mixture containing the [n-5]-hydroxy fatty acid wherein the [n-6]-position is a single bond produced by the above-described process, a treated matter of the reaction mixture or the [n-5]-hydroxy fatty acid wherein the [n-6]-position is a single bond isolated from the reaction mixture at 10 to 80° C., preferably 20 to 50° C., at pH 2 to 9, preferably pH 3 to 8, more preferably pH 4 to 7, for 12 hours to 7 days, preferably 1 to 4 days, most preferably 2 to 3 days. If necessary, an aqueous medium such as water may be added prior to the reaction.

The "treated matter of the reaction mixture containing the [n-5]-hydroxy fatty acid wherein the [n-6]-position is a single bond" refers to a treated matter containing the [n-5]-hydroxy fatty acid wherein the [n-6]-position is a single bond obtained in the process of isolation and purification of the reaction mixture containing the [n-5]-hydroxy fatty acid wherein the [n-6]-position is a single bond.

The above-described buffer, surfactant, organic solvent, antioxidant, etc. may be added to the reaction mixture as may be required.

When the cells of the microorganism are used, reaction is carried out in the following manner. A seed culture obtained by inoculating 1 to 3 loopfuls of the cells of the second microorganism into 5 to 50 ml of a medium containing carbon sources, nitrogen sources, etc., followed by stationary culture for 1–5 days, or another seed culture obtained by inoculating the above seed culture in an amount of 1 to 5% into 100 ml to 1 l of a medium, followed by stationary culture for 1 to 5 days, is inoculated in an amount of 0.1 to 50% into the reaction mixture containing the [n-5]-hydroxy fatty acid wherein the [n-6]-position is a single bond, followed by culturing under aerobic conditions, e.g., with aeration and stirring. There is no specific restriction as to the conditions of aeration and stirring, but it is preferred to carry out aeration at 0.01 to 3 vvm and stirring at 200 to 1200 rpm. Culturing may be carried out at any temperature that allows conversion of the [n-5]-hydroxy fatty acid wherein the [n-6]-position is a single bond into a δ-lactone, preferably 5 to 35° C. It does not matter whether the microorganism grows or not by the culturing. The culturing time varies depending upon the conditions, but it is usually 12 hours to 7 days.

After the completion of the reaction with the second microorganism or the culturing of the second microorganism, the reaction mixture or culture may be adjusted to pH 1 to 6, preferably pH 3 to 5, and further subjected to reaction at 5 to 80° C., preferably 20 to 35° C. for 30 minutes or more to increase the yield of δ-lactone. This method is preferably employed when *Saccharomyces cerevisiae, Kluyveromyces marxianus*, etc. are used as the second microorganism.

The δ-lactone can be isolated and purified from the reaction mixture or culture by conventional methods such as extraction with a solvent. That is, the δ-lactone can be isolated and purified by adding about 20 to 60 wt % pentane/ether mixture (5:95 to 80:20, v/v) and 20 to 60 wt % saturated aqueous solution of sodium chloride to about 0.2 to 10 ml of the reaction mixture or culture, followed by shaking for 10 minutes, and then centrifuging the resulting mixture to obtain the supernatant.

The δ-lactones can be determined, for example, by gas chromatography under the following conditions.

Apparatus: Gas chromatograph mass spectrometer GCMS-QP5000 (Shimadzu Corporation)

Column: TC-WAX 60 m 0.25 mm×0.25 μm

Helium flow rate: 0.5 ml/minute

Column temperature: 40° C. (0.5 minute)–5° C./minute–240° C. (69.5 minutes)

Pressure: 50 Kpa (0 minute)–5 Kpa/minute-300 Kpa (60 minutes)

Standard δ-lactone preparation: δ-decalactone (Aldrich), jasmine lactone (Nippon Zeon)

The reaction mixture or culture containing the δ-lactone obtained by the above-described process can be added to foods, etc., as such, or if necessary, after being sterilized or after removing solids therefrom by filtration. The purified δ-lactone can also be added to foods.

The δ-lactones may be added to any foods, preferably, milk beverages, processed milk products, processed animal food products, confectionery (e.g., cakes, ice cream and snacks) and seasonings (e.g., white sauces, cheese sauces and dressings).

The δ-lactones are usually added to foods at a concentration of ca. 0.1 to 100 ppm, preferably ca. 0.25 to 20 ppm.

Examples, Comparative Examples and Test Examples of the present invention are described below.

BEST MODES FOR CARRYING OUT THE INVENTION

In the following Examples, the measurement of FAB mass spectrum and high resolution FAB mass spectrum was carried out If using JMS-HX/HX110A (JEOL Ltd.), and the NMR measurement was carried out using JNM-A400(JEOL Ltd.) according to a conventional method.

EXAMPLE 1

Formation of Hydroxy Fatty Acids

Linoleic acid, γ-linolenic acid, α-linolenic acid, cis-11,cis-14-eicosadienoic acid, cis-8,cis-11,cis-14-eicosatrienoic acid, cis-11,cis-14,cis-17-eicosatrienoic acid, cis-13,cis-16-docosadienoic acid and cis-12-octadecenoic acid (0.5 g each, all produced by Sigma Chemical Co.) were respectively added to 100 ml of a nutrient medium comprising 0.18 g of yeast extract, 0.42 g of polypeptone and 0.62 ml of 60% liquid glucose (pH 6.5). To each of the resulting mixtures were added 0.02 ml of E-mix 80(Eisai Co., Ltd.) as an antioxidant and 2 g of skim milk powder as a dispersing agent, and 3 ml of a seed culture of *Pediococcus Pentosaceus* IFO3891 was inoculated therein, followed by culturing with stirring at 80 rpm at 25° C. for 2 days.

To 0.5 ml of each of the resulting cultures was added an equal amount of a chloroform/methanol mixture (2:1, v/v) as a solvent to extract lipid. The obtained lipid extract was spotted on TLC glass plate silica gel 60(No. 5721, Merck & Co., Inc.) in 5 µl portions. The first development was carried out using toluene/diethyl ether/ethanol/acetic acid (50:40:2:0.2, v/v/v/v) for 20 minutes, followed by drying of the plate, and the second development was carried out using hexane/diethyl ether (94:6, v/v) for 35 minutes, followed by drying of the plate. As a color developer, an appropriate amount of 8% (w/w) solution of phosphoric acid containing 6 g/100 ml copper acetate was sprayed on the development surface, followed by heating at 140° C. for 25 minutes.

The results are shown in Table 1.

TABLE 1

| Fatty acid | Rf value |
| --- | --- |
| Linoleic acid | 0.19 |
| γ-Linoleic acid | 0.17 |
| α-Linoleic acid | 0.16 |
| cis-11,cis-14-Eicosadienoic acid | 0.18 |
| cis-8,cis-11,cis-14-Eicosatrienoic acid | 0.18 |
| cis-11,cis-14,cis-17-Eicosatrienoic acid | 0.18 |
| cis-13,cis-16-Docosadienoic acid | 0.20 |
| cis-12-Octadecenoic acid | 0.19 |

As shown in Table 1, with every one of the fatty acids used, a hydroxy fatty acid was detected as a brown spot at an Rf value in the range of 0.13 to 0.22, which is the Rf value range expected for hydroxy fatty acids.

EXAMPLE 2

Production of a Hydroxide of Linoleic Acid

Linoleic acid (5 g) was added to 1000 ml of a nutrient medium comprising 1.8 g of yeast extract, 4.2 g of polypeptone and 6.2 ml of 60% liquid glucose (pH 6.5), and 0.2 ml of E-mix 80 as an antioxidant and 20 g of skim milk powder as a dispersing agent were added thereto. Into the resulting mixture was inoculated 30 ml of a seed culture of *Pediococcus pentosaceus* IFO3891, followed by culturing with stirring at 80 rpm at 25° C. for 2 days.

To ca. 1000 ml of the obtained culture was added ca. 120 wt % diethyl ether/toluene (4:5, v/v), followed by shaking for about 20 minutes, and the resulting mixture was centrifuged to separate the supernatant as a lipid extract. After the lipid extract was concentrated to ca. 50 ml with a rotary evaporator, column chromatography was carried out using a glass column having an inside diameter of 3.14 cm×50 cm packed with ca. 80 g of silica gel (Wako gel C-2000) in the following manner.

After the column was washed with 300 ml of the above solvent mixture, the concentrated lipid extract was added thereto. Then, 500 ml of the above solvent mixture was passed through the column at a flow rate of 3 ml/minute and the eluate was taken in 5 ml fractions. The lipid in each fraction was developed on a silica gel-precoated TLC plate, whereby 13-hydroxy-9-octadecenoic acid was detected and obtained.

[Physicochemical Properties of 13-hydroxy-9-octadecenoic acid]

(1) Molecular formula: $C_{18}H_{34}O_3$
(2) FAB mass spectrum: m/z 299(M+H)$^+$
(3) High resolution FAB mass spectrum: m/z 299.2592. (M+H)$^+$, Calculated for $C_{18}H_{35}O_3$: 299.2586
(4) $^{13}$C-NMR spectrum (100 MHz, CDCl$_3$): δ ppm (multiplicity), 179.2(s), 130.5(d), 129.3(d), 71.9(d), 37.4(t), 37.3(t), 34.0(t), 31.9(t), 29.7(t), 28.9(t), 28.9(t), 28.9(t), 27.1(t), 25.3(t), 24.7(t), 23.6(t), 22.6(t), 14.0(q)
(5) $^1$H-NMR spectrum (400 MHz, CDCl$_3$): δ ppm [integration, multiplicity, coupling constant J (Hz)], 5.38 (1H, m), 5.38(1H, m), 3.63(1H, m), 2.33(2H, t, 7.4), 2.12(2H, m), 2.04(2H, q, 6.5), 1.63(2H, m), 1.52(2H, m), 1.52(2H, m), 1.44(2H,m), 1.31(2H,m), 1.31(2H,m), 1.31 (2H,m), 1.31(2H, m), 1.31(2H, m), 1.31(2H, m), 0.89(3H, t, 6.8)

EXAMPLE 3

Production of a Hydroxide of α-linolenic Acid (13-hydroxy-9,15-octadecadienoic acid)

The same procedure as in Example 2 was repeated, except that linoleic acid was replaced by α-linolenic acid, whereby 13-hydroxy-9,15-octadecadienoic acid was obtained.

[Physicochemical Properties of 13-hydroxy-9,15-octadecadienoic acid]

(1) Molecular formula: $C_{18}H_{32}O_3$
(2) FAB mass spectrum: m/z 297(M+H)$^+$
(3) High resolution FAB mass spectrum: m/z 297.2421(M+H)$^+$, Calculated for $C_{18}H_{33}O_3$: 297.2430
(4) $^{13}$C-NMR spectrum (100 MHz, CDCl$_3$): δ ppm (multiplicity), 178.3(s), 135.2(d), 130.6(d), 129.2(d), 124.4(d), 71.3(d), 36.7(t), 35.3(t), 33.9(t), 29.5(t), 28.9(t), 28.9(t), 28.9(t), 27.1(t), 24.7(t), 23.7(t), 20.7(t), 14.3(q)
(5) $^1$H-NMR spectrum (400 MHz, CDCl$_3$): δ ppm [integration, multiplicity, coupling constant J (Hz)], 5.56 (1H, m), 5.38(1H, m), 5.37(1H, m), 5.37(1H, m), 3.65 (1H, m), 2.34(2H, t, 7.4), 2.23(2H, t, 7.1), 2.15(2H,m), 2.07(2H, m), 2.03(2H, m), 1.64(2H, m, 7.1), 1.54(2H, m), 1.32(2H, m), 1.32(2H, m), 1.32(2H, m), 1.32(2H, m), 0.97(3H, t, 7.4)

EXAMPLE 4

Production of a Hydroxide of γ-linolenic Acid (13-hydroxy-6,9-octadecadienoic acid)

The same procedure as in Example 2 was repeated, except that linoleic acid was replaced by α-linolenic acid, whereby 13-hydroxy-6,9-octadecadienoic acid was obtained.

[Physicochemical Properties of 13-hydroxy-6,9-octadecadienoic acid]
(1) Molecular formula: $C_{18}H_{32}O_3$
(2) FAB mass spectrum: m/z 297(M+H)$^+$
(3) High resolution FAB mass spectrum: m/z 297.2426(M+H)$^+$, Calculated for $C_{18}H_{33}O_3$: 297.2430
(4) $^{13}$C-NMR spectrum (100 MHz, CDCl$_3$): δ ppm (multiplicity), 178.6(s), 129.6(d), 129.4(d), 128.4(d), 128.4(d), 71.8(d), 37.4(t), 37.1(t), 33.9(t), 31.9(t), 28.9(t), 26.8(t), 25.6(t), 25.3(t), 24.4(t), 23.6(t), 22.6(t), 14.0(q)
(5) $^1$H-NMR spectrum (400 MHz, CDCl$_3$): δppm [integration, multiplicity, coupling constant J (Hz)], 5.38 (1H, m), 5.38(1H, m), 5.38(1H, m), 5.38(1H, m), 3.64 (2H, m), 2.80(2H, t, 5.6), 2.35(2H, t, 7.3), 2.18(2H, m), 2.09(2H, q, 7.5), 1.67(2H, m), 1.55(2H, m), 1.45(2H, m), 1.45(2H, m), 1.42(2H, m), 1.31(2H, m), 1.31(2H, m), 0.89(3H, t, 6.8)

EXAMPLE 5

Linoleic acid (0.5 g) was added to 100 ml of a nutrient medium comprising 0.18 g of yeast extract, 0.42 g of polypeptone and 0.62 ml of 60% liquid glucose (pH 6.5), and 0.02 ml of E-mix 80 as an antioxidant and 2 g of skim milk powder as a dispersing agent were added thereto. Into the resulting mixture was inoculated 3 ml of a seed culture of *Pediococcus pentosaceus* IFO3891 as the first microorganism, followed by culturing with stirring at 80 rpm at 25° C. for 2 days.

To 0.5 ml of the resulting culture was added an equal amount of a chloroform/methanol mixture (2:1, v/v) as a solvent to extract lipid. The obtained lipid extract was spotted on TLC glass plate silica gel 60 in 5 μl portions. The first development was carried out using toluene/diethyl ether/ethanol/acetic acid (50:40:2:0.2, v/v/v/v) for 20 minutes, followed by drying of the plate, and the second development was carried out using hexane/diethyl ether (94:6, v/v) for 35 minutes, followed by drying of the plate. As a color developer, an appropriate amount of 8% (w/w) solution of phosphoric acid containing 6 g/100 ml copper acetate was sprayed on the development surface, followed by heating at 140° C. for 25 minutes.

As a result, a hydroxy fatty acid converted from linoleic acid was detected as a brown spot at the position of 0.19 of Rf value.

EXAMPLE 6

α-Linolenic acid (0.5 g) was added to 100 ml of a nutrient medium comprising 0.18 g of yeast extract, 0.42 g of polypeptone and 0.62 ml of 60% liquid glucose (pH 6.5), and 0.02 ml of E-mix 80 as an antioxidant and 2 g of skim milk powder as a dispersing agent were added thereto. Into the resulting mixture was inoculated 3 ml of a seed culture of *Pediococcus pentosaceus* IFO3891 as the first microorganism, followed by culturing with stirring at 80 rpm at 25° C. for 2 days.

After the completion of the culturing, extraction of lipid from the culture and thin layer chromatography were carried out in the same manner as in Example 1 to detect a hydroxy fatty acid converted from α-linolenic acid.

As a result, the hydroxy fatty acid was detected as a brown spot at the position of 0.16 of Rf value.

EXAMPLE 7

γ-Linolenic acid (0.5 g) was added to 100 ml of a nutrient medium comprising 0.18 g of yeast extract, 0.42 g of polypeptone and 0.62 ml of 60% liquid glucose (pH 6.5), and 0.02 ml of E-mix 80 as an antioxidant and 2 g of skim milk powder as a dispersing agent were added thereto. Into the resulting mixture was inoculated 3 ml of a seed culture of *Pediococcus pentosaceus* IFO3891 as the first microorganism, followed by culturing with stirring at 80 rpm at 25° C. for 2 days.

After the completion of the culturing, extraction of lipid from the culture and thin layer chromatography were carried out in the same manner as in Example 1 to detect a hydroxy fatty acid converted from γ-linolenic acid.

As a result, the hydroxy fatty acid was detected as a brown spot at the position of 0.17 of Rf value.

EXAMPLE 8

Linoleic acid (5 g) was added to 1 l of a nutrient medium comprising 1.8 g of yeast extract, 4.2 g of polypeptone and 6.2 ml of 60% liquid glucose (pH 6.5), and 0.2 ml of E-mix 80 as an antioxidant and 20 g of skim milk powder as a dispersing agent were added thereto. Into the resulting mixture was inoculated 30 ml of a seed culture of *Pediococcus pentosaceus* IFO3891, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 245 ppm of δ-decalactone was obtained in the culture.

EXAMPLE 9

α-Linolenic acid (5 g) was added to 1 l of a nutrient medium comprising 1.8 g of yeast extract, 4.2 g of polypeptone and 6.2 ml of 60% liquid glucose (pH 6.5), and 0.2 ml of E-mix 80 as an antioxidant and 20 g of skim milk powder as a dispersing agent were added thereto. Into the resulting mixture was inoculated 30 ml of a seed culture of *Pediococcus pentosaceus* IFO3891, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 103 ppm of jasmine lactone was obtained in the culture.

EXAMPLE 10

To 930 ml of water was added 40 ml of corn oil (Ajinomoto Co., Inc.), and 0.2 ml of E-mix 80 as an antioxidant and 0.4 g of Lipase MY (Meito Sangyo Co., Ltd.) as a hydrolase were added thereto. The mixture was allowed to stand at 40° C. for 24 hours to cause hydrolysis. To the obtained hydrolyzed corn oil were added 20 g of skim milk powder, 1.8 g of yeast extract, 4.2 g of polypeptone and 6.2 ml of 60% liquid glucose, and the resulting mixture was adjusted to pH 6.5. Into the resulting mixture was inoculated 30 ml of a seed culture of *Pediococcus pentosaceus* IFO3891, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 392 ppm of δ-decalactone was obtained in the culture.

EXAMPLE 11

A seed culture of Pediococcus sp. IFO3778 (30 ml) was inoculated into a medium containing hydrolyzed corn oil prepared in the same manner as in Example 10, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 173 ppm of δ-decalactone was obtained in the culture.

EXAMPLE 12

A seed culture of *Bifidobacterium bifidum* JCM7002 (30 ml) was inoculated into a medium containing hydrolyzed corn oil prepared in the same manner as in Example 10, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 115 ppm of δ-decalactone was obtained in the culture.

EXAMPLE 13

A seed culture of *Pediococcus pentosaceus* IFO3891 (30 ml) was inoculated into a medium containing hydrolyzed corn oil prepared in the same manner as in Example 10, followed by culturing with stirring at 400 rpm at 25° C. for 2 days.

After the completion of the culturing, 30 ml of a seed culture of *Saccharomyces cerevisiae* Kyokai No. 701 was inoculated into the obtained culture, followed by culturing with stirring at 900 rpm under aeration at 1 vvm at 25° C. for 4 days.

As a result, 23 ppm of δ-decalactone was obtained in the culture. To the culture was added 90% lactic acid (Musashino Kagaku Kenkyusho Co., Ltd.) to adjust the culture to pH 3, and the resulting mixture was allowed to stand at 25° C. for 30 minutes for further reaction. As a result, 197 ppm of δ-decalactone was obtained in the reaction mixture.

EXAMPLE 14

A seed culture of *Pediococcus pentosaceus* IFO3891 (30 ml) was inoculated into a medium containing hydrolyzed corn oil prepared in the same manner as in Example 10, followed by culturing with stirring at 400 rpm at 25° C. for 2 days.

After the completion of the culturing, 30 ml of a seed culture of *Kluyveromyces marxianus* IFO1090 was inoculated into the obtained culture, followed by culturing with stirring at 900 rpm under aeration at 1 vvm at 25° C. for 4 days.

As a result, 378 ppm of δ-decalactone was obtained in the culture. To the culture was added 90% lactic acid to adjust the culture to pH 3, and the resulting mixture was allowed to stand at 25° C. for 30 minutes for further reaction.

As a result, 783 ppm of δ-decalactone was obtained in the reaction mixture.

EXAMPLE 15

To 465 ml of water was added 20 ml of corn oil (Ajinomoto Co., Inc.), and 0.1 ml of E-mix 80 as an antioxidant and 0.2 g of Lipase MY (Meito Sangyo Co., Ltd.) as a hydrolase were added thereto. The mixture was allowed to stand at 40° C. for 24 hours to cause hydrolysis. To the obtained hydrolyzed corn oil were added 10 g of skim milk powder, 0.9 g of yeast extract, 2.1 g of polypeptone and 3.1 ml of 60% liquid glucose, and the resulting mixture was adjusted to pH 6.5. Into the resulting mixture was inoculated 15 ml of a seed culture of *Pediococcus pentosaceus* IFO3891, followed by culturing with stirring at 400 rpm at 25° C. for 2 days.

After the completion of the culturing, the obtained culture was mixed with 500 ml of a seed culture of *Kluyveromyces marxianus* IFO1090 obtained by culturing in a nutrient medium for 2 days, and the resulting mixture was cultured with stirring at 900 rpm under aeration at 1 vvm at 25° C. for 2 days.

As a result, 502 ppm of δ-decalactone was obtained in the culture.

EXAMPLE 16

The culture obtained in Example 10 was sterilized at 85° C. for one minute, and 0.6 ml of the sterilized culture was added to 200 g of commercially available corn cream soup. The concentration of δ-decalactone in the soup was 1.18 ppm. As a result of the addition of δ-decalactone, corn cream soup having a mild milky taste was obtained.

EXAMPLE 17

The culture obtained in Example 10 was sterilized at 85° C. for one minute, and 0.3 ml of the sterilized culture was added to 200 ml of commercially available low fat milk. The concentration of δ-decalactone in the low fat milk was 0.59 ppm. As a result of the addition of δ-decalactone, the smell of milk powder was masked and low fat milk having an improved milk flavor was obtained.

EXAMPLE 18

Into 500 ml of soybean milk was inoculated 15 ml of *Pediococcus pentosaceus* IFO3891 as a lactic acid bacterium, followed by stationary culture at 25° C. for one day.

After the completion of the culturing, 15 ml of *Kluyveromyces marxianus* IFO1090 was inoculated into the obtained culture, followed by culturing with stirring at 900 rpm under aeration at 1 vvm at 25° C. for 2 days.

As a result, 2.7 ppm of δ-decalactone was obtained in the culture. Additionally, a grassy smell of the culture was masked and fermented soybean milk having an improved flavor was obtained.

Industrial Applicability

The present invention provides a process for producing [n-5]-hydroxy fatty acids (n is an even number of 10 or more) wherein the [n-6]-position is a single bond from straight-chain fatty acids having n carbon atoms wherein at least the [n-6]-position is a double bond. The present invention also provides a process for producing δ-lactones from straight-chain fatty acids having n carbon atoms (n is an even number of 10 or more) wherein at least the [n-6]-position is a double bond via [n-5]-hydroxy fatty acids wherein the [n-6]-position is a single bond. The present invention further provides a process for producing compositions containing δ-lactones from compositions containing straight-chain fatty acids having n carbon atoms (n is an even number of 10 or more) wherein at least the [n-6]-position is a double bond.

In accordance with the present invention, industrially useful δ-lactones can be readily produced in large amounts from fatty acids derived from inexpensive food materials such as linoleic acid, α-linolenic acid and γ-linolenic acid using cells or a culture of a microorganism or a treated matter thereof.

What is claimed is:

1. A process for producing δ-decalone, which comprises the steps of:
   (i) causing cells or a culture of a microorganism having the activity to convert linoleic acid to 13-hydroxy-9-octadecenoic acid and belonging to the genus Pediococcus or Bifidobacterium, or a treated matter thereof to act on linoleic acid or a composition containing linoleic acid to form 13-hydroxy-9-octadecenoic acid; and
   (ii) causing cells or a culture of a microorganism having the activity to β-oxidize 13-hydroxy-9-octadecenoic acid and belonging to the genus Kluyveromyces. Zygosaccharomyces, Pichia, or Saccharomyces, or a treated matter thereof to act on the formed 13-hydroxy-9-octadecenoic acid to form δ-decalactone; and
   (iii) recovering the formed δ-decalactone.

2. The process according to claim 1, wherein the microorganism in step (i) is *Pediococcus pentosaceus*.

3. The process according to claim 1, wherein the microorganism in step (i) is *Pediococcus pentosaceus* IFO3891.

4. The process according to claim 1, wherein the microorganism in step (i) is *Bifidobacterium bifidum*.

5. The process according to claim 1, wherein the microorganism in step (i) is *Bifidobacterium bifidum* JCM7002.

6. The process according to claim 1, wherein the microorganism in step (ii) is *Kluyveromyces marxianus, Kluyveromyces thermotolerans, Kluyveromyces wickerhamii, Zygosaccharomyces rouxii, Zygosaccharomyces bailii, Zygosaccharomyces cidri, Pichia jadinii* or *Saccharomyces cerevisiae*.

7. The process according to claim 1, wherein the microorganism in step (ii) is *Kluyveromyces marxianus* IFO1090, *Kluyveromyces thermotolerans* ATCC24177, *Kluyveromyces wickerhamii* ATCC24178, *Zygosaccharomyces rouxii* NFR2007, *Zygosaccharomyces bailii* ATCC8766, *Zygosaccharomyces cidri* ATCC46819, *Pichia jadinii* IFO0987 or *Saccharomyces cerevisiae* Kyokai No. 701.

8. A process for producing jasmine lactone, which comprises the of:
   (i) causing cells or a culture of a microorganism having an activity to convert α-linolenic acid 13-hydroxy-9,15-octadecadienoic acid and belonging to the genus Pediococcus or Bifidobacterium, or a treated matter thereof, to act on α-linolenic acid or a composition containing α-linolenic acid to form 13-hydroxy-9,15-octadecadienoic acid; and
   (ii) causing cells or a culture of a microorganism having an activity to beta oxidize 13-hydroxy-9,15-octadecadienoic acid and belonging to the genus Kluyveromyces, Zygosaccharomyces, Pichia, Saccharomyces, or a treated matter thereof, to act on the formed 13-hydroxy-9,15-octadecadienoic acid to form jasmine lactone; and
   (iii) recovering the formed jasmine lactane.

9. The process according to claim 8, wherein the microorganism in step (i) is *Pediococcus pentosaceus* or *Bifidobacterium bifidum*.

10. The process according to claim 8, wherein the microorganism in step (i) is *Pediococcus pentosaceus* IFO3891 or *Bifidobacterium bifidum* JCM7002.

11. The process according to claim 8, wherein the microorganism in step (ii) is *Kluyveromyces marxianus, Kluyveromyces thermotolerans, Kluyveromyces wickerhamii, Zygosaccharomyces rouxii, Zygosaccharomyces bailii, Zygosaccharomyces cidri, Pichia jadinii* or *Saccharomyces cerevisiae*.

12. The according to claim 8, wherein the microorganism in step (ii) is *Kluyveromyces marxianus* IFO1090, *Kluyveromyces thermotolerans* ATCC24177, *Kluyveromyces wickerhamii* ATCC24178, *Zygosaccharomyces rouxii* NFR2007, *Zygosaccharomyces bailii* ATCC8766, *Zygosaccharomyces cidri* ATCC46819, *Pichia jadinii* IFO0987 or *Saccharomyces cerevisiae* Kyokai No. 701.

* * * * *